United States Patent [19]

Hocker et al.

[11] 4,020,084

[45] Apr. 26, 1977

[54] CYCLIC AMINALS OF AROMATIC ALDEHYDES

[75] Inventors: Jurgen Hocker, Cologne; Rudolf Merten, Leverkusen, both of Germany

[73] Assignee: Bayer Aktiengesellschaft, Leverkusen, Germany

[22] Filed: Nov. 9, 1973

[21] Appl. No.: 414,482

[30] Foreign Application Priority Data

Nov. 11, 1972 Germany ............................ 2255290

[52] U.S. Cl. .................. 260/308 A; 260/297 B; 260/308 B; 260/309.7
[51] Int. Cl.² ....................................... C07D 249/00
[58] Field of Search ................... 260/308 A, 308 B

[56] References Cited

UNITED STATES PATENTS 2,700,044   1/1955   Sartori ........................... 260/308 B

FOREIGN PATENTS OR APPLICATIONS 44-8,980   4/1969   Japan ............................. 260/308 B
6,801,662   8/1968   Netherlands ................... 260/308 A

OTHER PUBLICATIONS

Riebsomer et al., Journ. Org. Chem., 13, pp. 807–814 (1948).

*Primary Examiner*—Ethel G. Love
*Attorney, Agent, or Firm*—Burgess, Dinklage & Sprung

[57] ABSTRACT

This invention relates to aminals of aromatic hydroxy-aldehydes and to a process for the production thereof. The compounds can be used in the production of dyes.

2 Claims, No Drawings

CYCLIC AMINALS OF AROMATIC ALDEHYDES

SUMMARY

It has been found that new animals of aromatic hydroxy(mercapto)-aldehydes can be obtained by reacting phenols or thiophenols with a tetra-aminoethylene corresponding to the general formula (I):

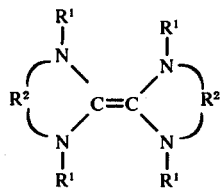

in which:

$R^1$ represents an optionally substituted aliphatic, aromatic or heterocyclic radical; and $R^2$ represents a saturated or unsaturated alkylene bridge having up to 3 carbon atoms, optionally substituted by lower alkyl groups, preferably with 1 to 4 carbon atoms, chlorine, $NO_2$ or CN, in addition to which a 5- or 6-membered cycloaliphatic ring or benzene ring may be fused to the alkylene bridge, at temperatures in the range of from $-20°$ to $+200°$ C, preferably at temperatures of from $50°$ to $180°$ C and more particularly at temperatures of from $100°$ to $160°$ C.

DESCRIPTION

Optionally substituted aliphatic radicals are those having up to 16 carbon atoms, preferably from 1 to 8 carbon atoms; these radicals may optionally contain up to 2 double bonds or a triple bond. Aliphatic radicals, of course, also include cycloaliphatic radicals having 5 to 12 carbon atoms and preferably 5 or 6 carbon atoms in the ring system.

Optionally substituted aromatic radicals are those having up to 14, preferably up to 10, and especially 6, carbon atoms in the ring system; in the case of the phenyl radical, it may even be attached through another phenyl radical, optionally by way even that of an oxygen or sulphur atom.

Optionally substituted heterocyclic radicals are those having from 5 to 7, preferably 5 or 6, ring members, the heterocyclic ring system optionally containing oxygen, nitrogen or sulphur as hetero atom, in which case this ring system may even be fused with a benzene ring.

Substituents on the aforementioned aliphatic, aromatic or heterocyclic radicals are, for example, aryl (preferably phenyl); CN; $NO_2$; alkylmercapto or alkoxy groups having preferably 1 to 4 carbon atoms; carboxylic ester groups, preferably those with lower aliphatic alcohols, preferably having up to 8 and, more particularly, up to 4 carbon atoms; and the disubstituted amino group, preferably, substituted by lower aliphatic radicals (preferably having 1 to 4 carbon atoms), halogens (preferably fluorine, chlorine or bromine), lower halogenated alkyl radicals (preferably 1 to 4 carbon atoms and preferably with fluorine and/or chlorine) and, in the case of the aromatic and heterocyclic radicals, even lower alkyl groups, preferably having 1 to 4 carbon atoms.

The majority of the (thio)-phenols used for the process according to the invention correspond to the general formula (II)

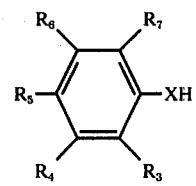

in which:

X represents oxygen (O) or sulphur (S); and $R^3$, $R^4$, $R^5$, $R^6$ and $R^7$ are the same or different and represent hydrogen; an optionally substituted aliphatic, aromatic, heterocyclic or araliphatic radical or any other radical which does not react with the tetra-aminoethylene used under the reaction conditions; or 2 adjacent radicals, together with the carbon atoms substituted thereby, forms a fused ring, at least one of the radicals $R^3$, $R^5$ or $R^7$ having to represent hydrogen.

The optionally substituted aliphatic, aromatic and heterocyclic radicals $R^3$, $R^4$, $R^5$, $R^6$ and $R^7$ have the same range of meanings as described above with reference to the radicals $R^1$, even in regard to their substituents.

In addition, two adjacent radicals ($R^3$ and $R^4$, $R^4$ and $R^5$, $R^5$ and $R^6$ or $R^6$ and $R^7$), together with the carbon atoms substituted by them, can form a preferably 5-, 6- or 7-membered fused ring, which can be carbocyclic or heterocyclic. Hetero atoms for this anellated ring include in particular oxygen, nitrogen and sulphur.

Araliphatic radicals ($R^3$ to $R^7$) are those which preferably contain the phenyl radical as aryl radical and which contain from 1 to 6 and preferably from 1 to 3 carbon atoms in the aliphatic portion. Substituents in the aromatic portion of the araliphatic ring include those referred to above in regard to the aromatic radical. The benzyl, phenylethyl, phenylpropyl radical and the 2- and 3-naphthylmethyl, -ethyl- and -propyl radicals are mentioned by way of example.

Examples of radicals which do not react with tetraaminoethylenes under the reaction conditions (radicals $R^3$ to $R^7$) include halogen (preferably fluorine, chlorine or bromine), cyano, nitro, hydroxyl, mercapto, alkylmercapto and alkoxy groups having 1 to 12, preferably 1 to 4 carbon atoms, carboxylic ester and sulphonic acid ester groups, preferably those with lower aliphatic alcohols (preferably with up to 8 and more particularly with up to 4 carbon atoms) and the amino group which can preferably be substituted either once or twice by substituents, such as, in particular, alkyl-, alkylcarbonyl and aryl radicals, preferably lower alkyl and alkylcarbonyl radicals with 1 to 8, especially 1 to 4 carbon atoms and the phenyl radical.

The new animals of aromatic hydroxy-(mercapto)-aldehydes obtainable by the process according to the invention correspond to the general formula (III):

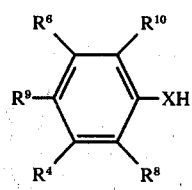

in which:

X, $R^4$ and $R^6$ are as defined above; and $R^8$, $R^9$ and $R^{10}$ are the same or different and either
a. represent the radical (IV):

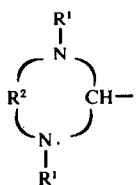
(IV)

in which:
$R^1$ and $R^2$ are as defined above, at least one of the radicals $R^8$, $R^9$ or $R^{10}$ having to represent this radical; or
b. $R^8$ has the same meaning as $R^3$, $R^9$ has the same meaning as $R^5$ and $R^{10}$ has the same meaning as $R^7$.

In particular, it is possible by the process according to the invention to obtain new compounds corresponding to the general formula (V):

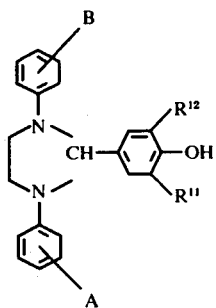
(V)

in which
A and B are the same or different and represent hydrogen, chlorine, the nitro group, alkoxy or lower alkyl, preferably having up to 4 carbon atoms,
$R^{11}$ and $R^{12}$ are the same or different and represent hydrogen, halogen, the nitro group, alkoxy, preferably lower alkyl having up to 6 carbon atoms or an optionally substituted amino group.

New compounds corresponding to the general formula (VI):

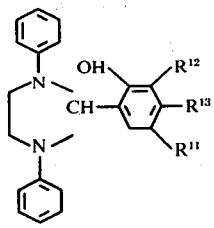
(VI)

in which:
$R^{11}$ and $R^{12}$ are as defined above; and
$R^{13}$ represents hydrogen or an optionally substituted amino group, can also be obtained advantageously by the process according to the invention.

Under certain conditions, for example in cases where phenol is used as starting material, the hydrogen of the phenolic hydroxyl group can even be substituted during the reaction by the radical (IV) as defined above.

It is also possible to obtain two-fold substitution of the (thio)-phenol used. For this purpose, tetra-aminoethylene and (thio)-phenol are preferably introduced into the reaction in a molar ratio of 1:1.

The process according to the invention is explained by way of example by the following reaction schemes:

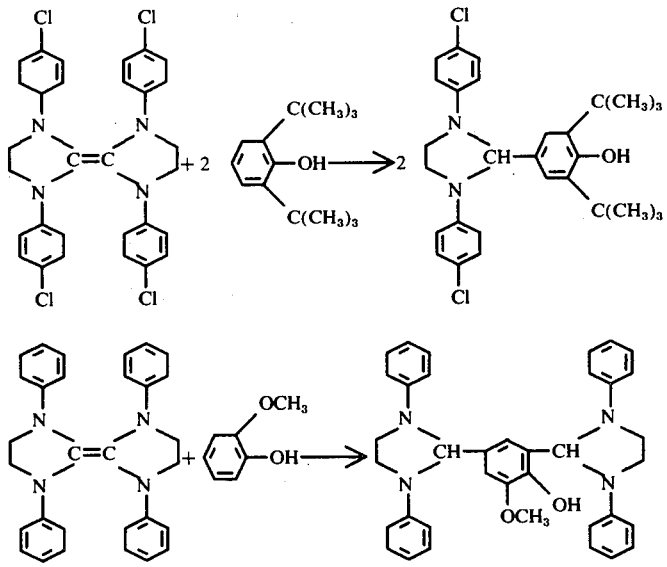

The tetra-aminoethylenes used for the process according to the invention are known or can be obtained by known methods. (Chem. Ber. 96, 1208 (1963), Bull. Chem. Soc. Japan, 44, 2171 (1971), Receuil 88, 289 (1969). The (thio)-phenols used for the process are known from the literature.

The process according to the invention for producing the new animals of aromatic hydroxy-(mercapto)-aldehydes is generally carried out as follows:

In general, the (thio)-phenol is employed in the stoichiometrically necessary quantity per mol of the tetraaminoethylene used. However, it is also possible to use an excess of one of the two starting materials.

In general, the reaction is best carried out in a solvent or diluent, in which case the starting materials can be dissolved or merely suspended. It is, of course, also possible to carry out the reaction in the absence of a solvent or diluent. The reaction is generally carried out by heating the starting materials to the selected reaction temperature, optionally in the presence of the solvent or diluent, and keeping the reaction mixture for a while at the selected reaction temperature.

In general, it is best to carry out the reaction in the absence of atmospheric oxygen, i.e. in an inert-gas atmosphere (for example a noble gas or carbon dioxide, but preferably nitrogen).

It can be advantageous, especially in cases where readily volatile solvents or diluents are used, to carry out the reaction under pressures higher than normal pressure, for example under a pressure of up to 10, preferably up to 5 atmospheres.

The following represent preferred tetra-aminoethylenes for carrying out the process according to the invention:
bis-[1,3-diaryl-imidazolidin-(2)-ylidenes], such as for example
bis-[1,3-diphenyl-imidazolidin-(2)-ylidene],
bis-[1,3-di-(4-methylphenyl)-imidazolidin-(2)-ylidene],
bis-[1,3-di-(3-methylphenyl)-imidazolidin-(2)-ylidene],
bis-[1,3-di-(2-methylphenyl)-imidazolidin-(2)-ylidene],
bis-[1,3-di-(4-methoxyphenyl)-imidazolidin-(2)-ylidene],
bis-[1,3-di-(3-methoxyphenyl)-imidazolidin-(2)-ylidene],
bis-[1,3-(2-methoxyphenyl)-imidazolidin-(2)-ylidene],
bis-[1,3-di-(4-chlorophenyl)-imidazolidin-(2)-ylidene], or bis-[1,3-di-α-(β)-naphthyl-imidazolidin-(2)-ylidene] and substitution products thereof,
bis-[1,3-dialkyl imidazolidin-(2)-ylidenes] such as, for example, bis-[1,3-diethyl imidazolidin-(2)-ylidene].

The following are mentioned as examples of optionally substituted (thio)-phenols which can be used for the process according to the invention:
phenol, thiophenol, 2-chlorophenol, 3-chlorophenol, 4-chlorophenol, 2,4-dichlorophenol, 2,6-dichlorophenol, trichlorophenols, 2-nitrophenol, 3-nitrophenol, 4-nitrophenol, dinitrophenols, 4-chloro-2-nitrophenol, 4-chloro-3-nitrophenol, 2-chloro-4-nitrophenol, 3-chloro-4-nitrophenol, 4,6-dichloro-3-nitrophenol, 4-chlorothiophenol, 2-hydroxytoluene, 3-chloro-2-hydroxy-toluene, 4-chloro-2-hydroxytoluene, 5-chloro-2-hydroxy-toluene, 6-chloro-2-hydroxytoluene, 3-nitro-2-hydroxytoluene 4-nitro-2-hydroxytoluene 3-hydroxytoluene, 4-chloro-3-hydroxytoluene, 6-chloro-3-hydroxytoluene, 4-nitro-3-hydroxytoluene, 6-nitro-3-hydroxytoluene, 4-hydroxytoluene 3-nitro-4-hydroxytoluene, 4-mercaptotoluene, 2-hydroxy-1-ethylbenzene, 3-hydroxy-1,2-dimethylbenzene, 4-hydroxy-1,2-dimethylbenzene, 2-hydroxy-1,3-dimethylbenzene, 4-hydroxy-1,3-dimethylbenzene, 5-hydroxy-1,3-dimethylbenzene, 2-chloro-5-hydroxy-1,3-dimethylbenzene, 2-hydroxy-1,4-dimethylbenzene, 5-hydroxy-1-methyl-3-ethylbenzene, 6-hydroxy-1,2,4-trimethylbenzene, 2-hydroxy-1-tert.-butylbenzene, 5-hydroxy-1-methyl-3-isopropylbrnzene, 2-hydroxy-1,3-diisopropylbenzene, 2-hydroxy-1,3-di-tert.-butylbenzene, 6-hydroxy-1,2,3,4-tetrahydronaphthalene, 1-hydroxy-naphthalene, 2-hydroxynaphthalene, 2-hydroxybiphenyl, 1,2-dihydroxybenzene, 2-methoxyphenol, 1,3-dihydroxybenzene, 3-methoxyphenol, 1,4-dihydroxybenzene, 4-methoxyphenol, salicylic acid methyl ester, 3-hydroxybenzoic acid ethyl ester, 4-hydroxybenzoic acid methyl(ethyl)ester, 2-acetylaminophenol, 3-dimethylaminophenol, 3-ethylaminophenol, 3-diethylaminophenol, 4-methylaminophenol, 4-dimethylaminophenol, 6-dimethylamino-3-hydroxtoluene, 2-dimethylamino-4-hydroxytoluene, 3-[2H-naphtho[1.2-d]triazo-2-yl]-phenol, 3-[4-methyl-5-phenyltriazol-2-yl]-phenol.

In cases where the process is carried out in the presence of solvents, the solvents used should be inert towards the reactants. Examples of suitable solvents include aromatic hydrocarbons, such as benzene or mesitylene, chlorinated aromatic hydrocarbons such as chlorobenzene or o-dichlorobenzene, and aliphatic hydrocarbons such as chloroform or carbon tetrachloride, and also dimethylformamide and acetonitrile.

The new animals of aromatic hydroxy-(mercapto)-aldehydes obtainable by the process according to the invention are valuable intermediate products and can be used for the production of plant protection agents and dyes, although they can even be directly used as such. Cyclic animals of aromatic hydroxy aldehydes are important starting materials for the synthesis of phenol aldehydes, some of which are extremely difficult to obtain by other methods and which, for their part, play an important role inter alia in the odorant and dyestuffs industry.

Hydrolysis of the new animals of aromatic hydroxy-(mercapto)-aldehydes into the corresponding hydroxy-(mercapto)-aldehydes can be carried out by conventional methods, both in the presence of alkaline catalysts and, preferably, also in the presence of acid catalysts. In many cases, there is no need to isolate the intermediate aminal.

The use of hydroxy-(mercapto)-aldehydes obtained by hydrolysis is known (cf. U.S. Pat. Nos. 3,503,732 and 3,585,243; DOS No. 2,009,504; Japanese Patent Application No. 70 620/66 and Russian Pat. Nos. 264,387 and 270,989).

In the following Examples, temperatures are given in ° C, parts by weight are generally grammes and parts by volume are millilitres.

The abbreviations IR, MS and NMR stand for infrared spectrum, mass spectrum and nuclear-magnetic-resonance spectrum. The band associated with the OH-group is indicated in the infrared spectrum, the masses are determined in the mass spectrum and the chemical displacement in $\delta$/ppm is determined in the nuclear-resonance spectrum; a small letter in brackets after the $\delta$-value and in the corresponding formula denotes the proton for which the displacement is quoted, whilst a capital letter indicates whether a singlet (S), doublet (D), triplet (T), quartet (Q) or multiplet (M) is involved.

In the elemental analyses, the percent symbols have been left out in accordance with standard practice.

EXAMPLE 1

4.44 Parts by weight of bis-[1,3-diphenyl-imidazolidin-(2)-ylidene] and 2.44 parts by weight of 2,6-dimethylphenol in 15 parts by volume of dimethylformamide are heated for 10 minutes under nitrogen to boiling point. Part of the solvent is removed in vacuo. The compound 4-hydroxy-3,5-dimethyl-1-(1,3-diphenyl-2-imidazolidinyl)-benzene (I), m.p. 166°–167° C (from i-isopropanol), is obtained in a yield of 5.0 parts by weight.

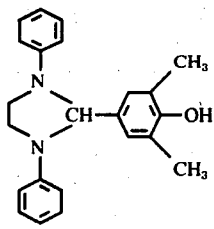

I

Analysis: calculated: C 80.18 H 7.02 N 8.13; found: 80.2 7.1 8.3; IR: 3557 cm$^{-1}$.

EXAMPLE 2

4.44 Parts by weight of bis-[1,3-diphenyl-imidazolidin-(2)-ylidene] and 4.12 parts by weight of 2,6-di-tert.-butylphenol in 15 parts by volume of dimethylforamide are heated for 15 minutes under nitrogen to boiling point. The solvent is removed in vacuo and the residue is rubbed with petroleum ether. 4-hydroxy-3,5-di-tert.-butyl-1-(1,3-diphenyl-2-imidazolidinyl)-benzene (II), m.p. 144° C (from acetonitrile), is obtained in a yield of 7.2 parts by weight.

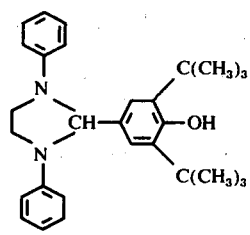

II

Analysis: calculated: C 81.26 H 8.47 N 6.54; found: 81.2 8.6 6.5; IR: 3605 cm$^{-1}$.

EXAMPLE 3

4.44 parts by weight of bis-[1,3-diphenyl-imidazolidin-(2)-ylidene] and 4.12 parts by weight of 2,6-di-tert.-butylphenol in 20 parts by volume of mesitylene are heated for 150 minutes under nitrogen to boiling point. The solvent is removed in vacuo, and the residue is suspended in a little cold i-propanol and filtered. 5.6 parts by weight of 4-hydroxy-3,5-di-tert.-butyl-1-(1,3-diphenyl-2-imidazolidinyl)-benzene (II) are obtained in a yield of 5.6 parts by weight.

EXAMPLE 4

5.82 parts by weight of bis-[1,3-di-(4-chlorophenyl)-imidazolidin-(2)-ylidene] and 4.12 parts by weight of 2,6-di-tert.-butylphenol in 15 parts by volume of dimethylformamide are heated for 10 minutes under nitrogen to boiling point. Part of the solvent is removed in vacuo. 4-hydroxy-3,5-di-tert.-butyl-1-[1,3-di-(4-chlorophenyl)-2-imidazolidinyl]-benzene (III), m.p. 220°–222° C (from acetonitrile), is obtained in a yield of 8.8 parts by weight.

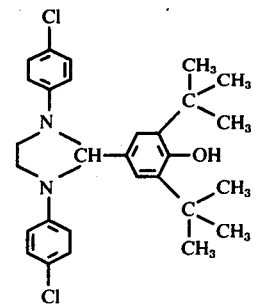

III

Analysis: calculated: C 70.01 H 6.89 N 5.64; found: 70.4 6.9 5.5; IR: 3615 cm$^{-1}$.

EXAMPLE 5

4.44 Parts by weight of bis-[1,3-diphenyl imidazolidin-(2)-ylidene] and 2.78 parts by weight of 2-nitrophenol in 15 parts by volume of dimethylformamide are heated under nitrogen for 15 minutes to boiling point. The solvent is removed in vacuo, and the oily residue is taken up in chloroform and purified through a silica gel column. 4-hydroxy-3-nitro-1-(1,3-diphenyl-2-imidazolidinyl)-benzene (IV) is obtained in the form of a pale yellow substance which crystallises with difficulty:

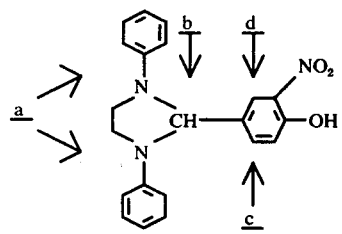

IV

IR: 3200 cm$^{-1}$;
MS: 361 (M$^+$), 284, 255, 223, 139, 106, 91, 77;
NMR: 3.82 (a,M), 6.01 (b,S), 7.66 (c,Q), 8.23 (d,D).

EXAMPLE 6

4.44 Parts by weight of bis-[1,3-diphenyl imidazolidin-(2)-ylidene] and 3.26 parts by weight of 2,6-dichlorophenol in 15 parts by volume of dimethylformamide are heated for 5 minutes under nitrogen to 130° C. The solvent is then removed in vacuo, and the residue is rubbed with i-propanol, followed by filtration under suction. 4-hydroxy-3,5-dichloro-1-(1,3-diphenyl-2-imidazolidinyl)-benzene (V) is obtained in a yield of 5.0 parts by weight.

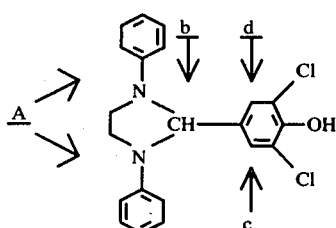

V

IR: 3480 cm$^{-1}$;
MS: 384 (M$^+$), 278, 223, 106, 104, 91, 77;

NMR: 3.92 (a,M), 6.33 (b,S) 7.74 (c,S).

EXAMPLE 7

44.4 Parts by weight of bis-[1,3-diphenyl imidazolidin-(2)-ylidene] and 28.5 parts by weight of 3-chloro-2-hydroxytoluene in 150 parts by volume of dimethylformamide are heated for 10 minutes under nitrogen to boiling point. The solvent is removed in vacuo and the residue is rubbed with a little i-propanol. 4-hydroxy-3-chloro-5-methyl-1-(1,3-diphenyl-2-imidazolidinyl)-benzene (VI), m.p. 146°–147° C (from i-propanol), is obtained in a yield of 60 parts by weight.

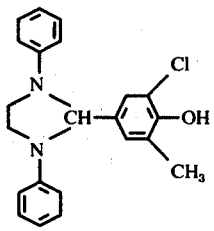

VI

Analysis: calculated: C 72.42 H 5.80 N 7.68; found: 72.3 6.1 7.7.

EXAMPLE 8

4.44 Parts by weight of bis-[1,3-diphenyl imidazolidin-(2)-ylidene] and 3.06 parts by weight of 3-nitro-2-hydroxytoluene in 15 parts of volume of dimethylformamide are heated for 5 minutes under nitrogen to boiling point. The solvent is removed in vacuo, and the residue is taken up in chloroform and purified through a silica gel column. The pale yellow compound, 4-hydroxy-3-methyl-5-nitro-1-(1,3-diphenyl-2-imidazolidinyl)-benzene (VII), is obtained.

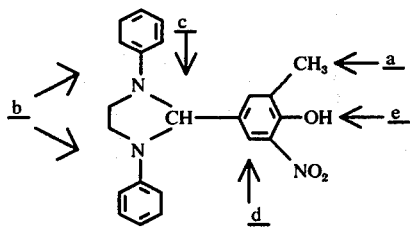

VII

IR: 3320 cm$^{-1}$; NMR: 2.22 (a,S), 3.80 (b,M), 5.92 (c,S), 8.02 (d,D), 10.75 (e, wide) MS: 385 (M$^+$), 298, 269, 223, 153, 107, 91, 77.

EXAMPLE 9

4.44 Parts by weight of bis-[1,3-diphenyl imidazolidin-(2)-ylidene] and 3.56 parts by weight of 2,6-diisopropylphenol in 15 parts by volume of dimethylformamide are heated for 15 minutes under nitrogen to boiling point. After the solvent has been removed in vacuo, the compound 4-hydroxy-3,5-diisopropyl-1-(1,3-diphenyl-2-imidazolidinyl)-benzene is obtained in the form of colourless crystals, melting at 116°–118° C (from i-propanol) (VIII).

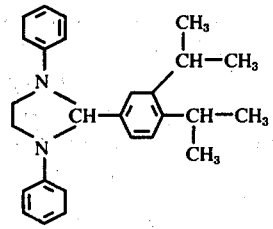

VIII

Analysis: calculated: C 80.97 H 8.05 N 7.0; found: 80.6 8.1 7.0;
IR: 3586 cm$^{-1}$.

EXAMPLE 10

4.44 Parts by weight of bis-[1,3-diphenyl imidazolidin-(2)-ylidene] and 1.88 parts by weight of phenol in 15 parts by volume of dimethylformamide are heated under nitrogen for 30 minutes to boiling point. The reaction mixture is cooled, filtered off under suction after a while and 4-(1,3-diphenyl-2-imidazolidinyloxy)-1-(1,3-diphenyl-2-imidazolidinyl)-benzene (IX) is obtained in the form of colourless crystals, melting at 218°–221° C (from acetonitrile).

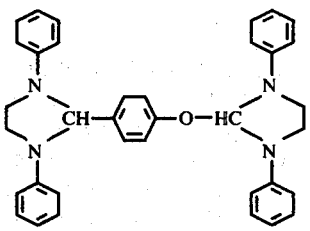

IX

Analysis: calculated: C 80.26 H 6.30 N 10.40; found: 80.6 6.6 10.6;
MS: (M$^+$), 433, 419, 313, 223, 107, 91, 77.

EXAMPLE 11

8.88 parts by weight of bis-[1,3-diphenyl imidazolidin-(2)-ylidene] and 2.48 parts of guaiacol in 30 parts by volume of dimethylformamide are heated for 60 minutes under nitrogen to boiling point. Part of the solvent is removed in vacuo. 4-hydroxy-3-methoxy-1,5-bis-(1,3-diphenyl-2-imidazolidinyl)-benzene (X), melting at 242° C (from nitrobenzene), is obtained in yield of 8.5 parts by weight

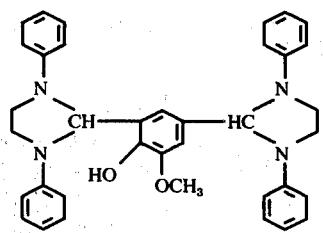

X

Analysis: calculated: C 78.14 H 6.38 N 9.85; found: 78.2 6.4 9.9
IR: 3400 cm$^{+1}$.

EXAMPLE 12

4.44 Parts by weight of bis-[1,3-diphenyl imidazolidin-(2)-ylidene] and 2.44 parts by weight of 2,4-dimethylphenol in 15 parts of volume of dimethylformamide are heated under nitrogen for 160 minutes to boiling point. Part of the solvent is removed in vacuo. 2-Hydroxy-3,5-dimethyl-1-(1,3-diphenyl-2-imidazolidinyl)-benzene (XI), which contains 1 mol of dimethylformamide and melts at 75° (from dimethylformamide), is obtained in a yield of 3.0 parts by weight.

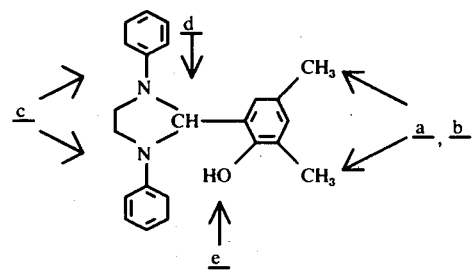

XI

IR: 3200 cm$^{-1}$; NMR: 2.12 (a,S), 2.20 (b,S), 3.68 (c,M), 6.10 (d,s) 8.50 (e,wide).

EXAMPLE 13

4.44 Parts by weight of bis-[1,3-diphenyl imidazolidin-(2)-ylidene] and 2.9 parts by weight of 8-hydroxyquinoline in 15 parts by volume of toluene are heated for 6.5 hours under nitrogen to boiling point. The solid reaction product is then filtered off under suction, giving 5.6 parts by weight of 8-hydroxy-5-(1,3-diphenyl-2-imidazolidinyl)-quinoline (XII), melting at 190°–196° C.

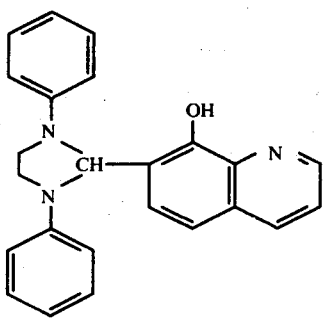

XII

IR: 3350 cm$^{-1}$; Analysis: calculated C 78.44 H 5.76 N 11.44; found: 78.5 5.6 11.0.

EXAMPLE 14

4.44 parts by weight of bis-[1,3-diphenyl-imidazolidin-(2)-ylidene] and 1.24 parts by weight of 3-methoxyphenol in 15 parts by volume of dimethylformamide are heated under nitrogen for 15 minutes to boiling point. The solvent is then removed, partly in vacuo, and the reaction product obtained is filtered off under suction. The bisaminal (XIII) of m.p. 195° C is obtained in a yield of 2.5 parts by weight.

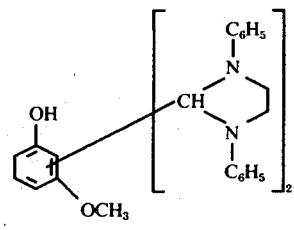

XIII

MS: 568 (M$^+$), 450, 343, 252, 223, 212, 107.

EXAMPLE 15

4.44 Parts by weight of bis-[1,3-diphenyl imidazolidin-(2)-ylidene] and 3.02 parts by weight of 2-dimethylamino-4-hydroxytoluene in 10 parts by volume of dimethylformamide are heated under nitrogen for 30 minutes to boiling point. After cooling, the solid reaction product is filtered off under suction, giving 3.5 parts by weight of 2-hydroxy-4-dimethylamino-5-methyl-1-(1,3-diphenyl-2-imidazolidinyl)-benzene (XIV), m.p. 207°– 212° C.

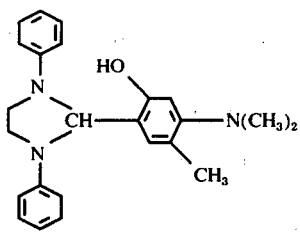

XIV

Analysis: calculated: C 77.18 H 7.29 N 11.26; found: 77.1 7.2 11.5

EXAMPLE 16

4.44 Parts by weight of bis-[1,3-diphenyl imidazolidin-(2)-ylidene] and 2.74 parts by weight of 3-dimethylaminophenol in 15 parts by volume of dimethylformamide are heated under nitrogen for 1.5 hours to boiling point. After cooling, the solid reaction product is filtered off under suction, giving 3.7 parts by weight of 2-hydroxy-4-dimethylamino-1-(1,3-diphenyl-2-imidazolidinyl)-benzene (XV) of m.p. 161° – 165° C (from acetonitrile).

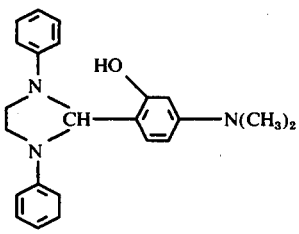

XV

Analysis: calculated: C 74.97 H 7.05 N 13.99; found: 75.5 7.0 13.6.

EXAMPLE 16a

The reaction product (XV) obtained in accordance with Example 16 is suspended in warm ethanol. A clear solution is formed, following the addition of 5 ml of 5% aqueous hydrochloric acid. 10 ml of water are added and the aqueous solution is extracted by repeated shaking with 10 ml batches of chloroform. After the chloroform has been distilled off in vacuo from the combined chloroform extracts, 2-hydroxy-4-dimethylaminobenzaldehyde (XVI) is obtained in the form of pale yellow needles, melting at 77° to 78° C.

EXAMPLE 17

4.44 Parts by weight of bis-[1,3-diphenyl imidazolidin-(2)-ylidene] and 2.61 parts by weight of 3-[2H-naphtho[1,2-d] triazol-(2)-yl]-phenol in 7 parts by weight of dimethylformamide are heated under nitrogen for 2 hours to boiling point. After cooling, 10 ml of ether are added and the solid reaction product is filtered off under suction, giving 3.8 parts by weight of the aminal (XVII), m.p. 193° C.

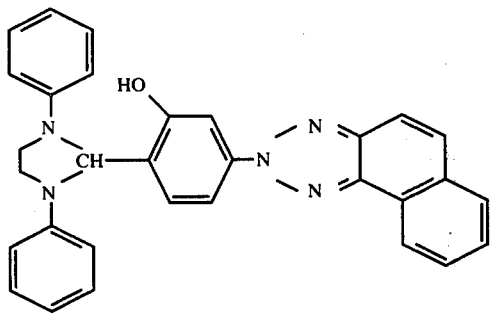

XVII

After recrystallisation from acetonitrile, the resulting crystallisate contains 1 mol of acetonitrile per mol of (XVII)

Analysis: calculated: C 75.57 H 5.39 N 16.03; found: 75.4 5.4 16.0.

EXAMPLE 17a 3.5 Parts by weight of the aminal (XVII) are suspended in 35 parts by volume of ethanol, followed by the addition at 60° C of 70 parts by volume of 5% aqueous hydrochloric acid. After cooling, the solid reaction product is filtered off, giving 1.7 parts by weight of the salicyl aldehyde (XVIII).

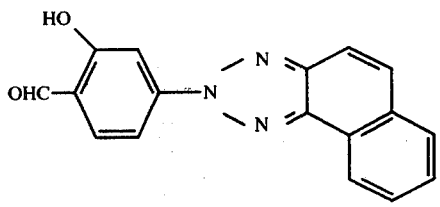

XVIII

EXAMPLE 18

125.5 parts by weight of 3-[4-methyl-5-phenyltriazol-(2)-yl]-phenol and 156 parts by weight of bis-[1,3-diphenyl imidazolidin-(2)-ylidene] in 300 parts by volume of absolute dimethylformamide are heated under nitrogen for 30 minutes to boiling point. After cooling, 150 parts by volume of ether are added and the solid reaction product is filtered off under suction, giving 158 parts by weight of the aminal (XIX).

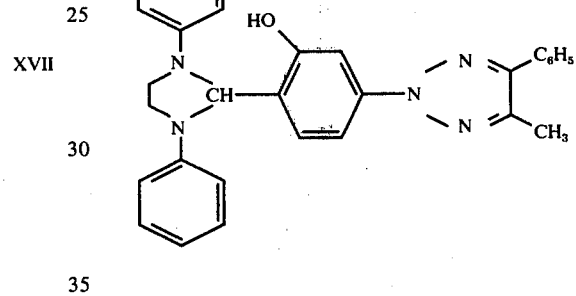

XIX

EXAMPLE 18a 158 parts by weight of the aminal (XIX) are suspended in 1550 parts by volume of ethanol. 950 parts by volume of 5% aqueous hydrochloric acid are added dropwise with stirring at 40° C. Stirring is continued for another 10 minutes, after which 1200 parts by volume of water are added. Filtration of the solid reaction product under suction gives 82 parts by weight of 4-[4-methyl-5-phenyl-1,2,3-triazol-(2)-yl]-salicyl aldehyde (XX).

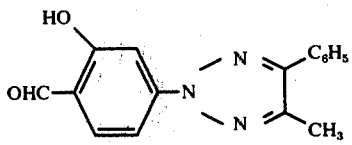

XX

What is claimed is:
1. 2-Hydroxy-4-[4-methyl-5-phenyl-triazol-(2)-yl]-(1,3-diphenyl-2-imidazolidinyl)-benzene.
2. 2-hydroxy-4-[2H-naphto [1,2-d]-triazol-(2)-yl]-(1,3-diphenyl-2-imidazolidinyl)-benzene.

* * * * *

UNITED STATES PATENT AND TRADEMARK OFFICE
CERTIFICATE OF CORRECTION

PATENT NO. : 4,020,084
DATED : April 26, 1977
INVENTOR(S) : Jurgen Hocker et al

It is certified that error appears in the above–identified patent and that said Letters Patent are hereby corrected as shown below:

Column 1, line 44, "that" should read -- then --.

Column 10, line 67, "$cm^{+1}$" should read -- $cm^{-1}$ --.

Signed and Sealed this fifth Day of July 1977

[SEAL]

Attest:

RUTH C. MASON
*Attesting Officer*

C. MARSHALL DANN
*Commissioner of Patents and Trademarks*